(12) United States Patent
Becker et al.

(10) Patent No.: US 10,802,033 B2
(45) Date of Patent: Oct. 13, 2020

(54) METHOD FOR MEASURING A PLURALITY OF STATUS PARAMETERS OF A FLUID CONTAINED IN A CONTAINER

(71) Applicant: Sartorius Stedim Biotech GmbH, Goettingen (DE)

(72) Inventors: Mario Becker, Goettingen (DE); Gerhard Greller, Goettingen (DE); Christian Grimm, Heiligenstadt (DE); Thorsten Adams, Goettingen (DE); Lars Boettcher, Melsugen (DE); Henry Weichert, Westewitz (DE)

(73) Assignee: Sartorius Stedim Biotech GmbH (DE)

( * ) Notice: Subject to any disclaimer, the term of this patent is extended or adjusted under 35 U.S.C. 154(b) by 243 days.

(21) Appl. No.: 15/736,030

(22) PCT Filed: Apr. 27, 2016

(86) PCT No.: PCT/EP2016/000679
§ 371 (c)(1),
(2) Date: Dec. 13, 2017

(87) PCT Pub. No.: WO2017/005333
PCT Pub. Date: Jan. 12, 2017

(65) Prior Publication Data
US 2018/0188274 A1    Jul. 5, 2018

(30) Foreign Application Priority Data

Jul. 6, 2015    (DE) .................. 10 2015 110 893

(51) Int. Cl.
*G01N 35/00*    (2006.01)
*C12M 1/00*    (2006.01)
(Continued)

(52) U.S. Cl.
CPC ... *G01N 35/00623* (2013.01); *B01F 15/0085* (2013.01); *B01F 15/00129* (2013.01);
(Continued)

(58) Field of Classification Search
CPC ................................ G01N 35/00623
(Continued)

(56) References Cited

U.S. PATENT DOCUMENTS

2006/0103394 A1    5/2006    Kita et al.
2008/0116378 A1*   5/2008    Frodl ................. G01N 21/3504
                                                250/338.5
(Continued)

FOREIGN PATENT DOCUMENTS

CN           1773299       5/2006
CN         101103265      1/2008
(Continued)

OTHER PUBLICATIONS

Translation of CN203329082U accessed from ESPACENET on Aug. 26, 2020 (Year: 2020).*

(Continued)

*Primary Examiner* — Christopher Adam Hixson
*Assistant Examiner* — Emily R. Berkeley
(74) *Attorney, Agent, or Firm* — Gerald E. Hespos; Michael J. Porco; Matthew T. Hespos

(57) ABSTRACT

A method is provided for measuring status parameters of a fluid contained in a container (10). The container (10) is configured for single use and has a wall on which a sensor-carrier plate is fixed in a fluid-tight manner. The plate carries sensors (S1-S5) that are in operative contact with the internal chamber of the container (10) and connected for data exchange (14) with an external control unit (16) that receives and processes the measurement data from the sensors (S1-S5). The sensor plate also carries a temporarily (Continued)

inactive duplicate (D1-D5) of at least one of the sensors (S1-S5) that is activated if measurement data of the sensor (S1-S5) is classified as atypical in the context of an integrity or plausibility test carried out by the external control unit (16).

9 Claims, 2 Drawing Sheets

(51) Int. Cl.
*C12M 1/36* (2006.01)
*G01D 3/10* (2006.01)
*B01F 15/00* (2006.01)

(52) U.S. Cl.
CPC ............ *C12M 23/14* (2013.01); *C12M 23/28* (2013.01); *C12M 41/48* (2013.01); *G01D 3/10* (2013.01)

(58) Field of Classification Search
USPC ........................................................ 422/68.1
See application file for complete search history.

(56) References Cited

U.S. PATENT DOCUMENTS

| | | |
|---|---|---|
| 2008/0128277 A1 | 6/2008 | Fukuda |
| 2011/0217573 A1 | 9/2011 | Kritzer et al. |
| 2012/0091326 A1 | 4/2012 | Baumfalk et al. |
| 2013/0084030 A1 | 4/2013 | Staheli et al. |
| 2014/0054186 A1 | 2/2014 | Riechers et al. |

FOREIGN PATENT DOCUMENTS

| | | |
|---|---|---|
| CN | 203329082 | 12/2013 |
| CN | 203416290 | 1/2014 |
| CN | 203929257 | 11/2014 |
| DE | 10 2006 054 165 | 4/2008 |
| EP | 2 365 575 | 9/2011 |
| EP | 2 503 320 | 10/2014 |
| EP | 2 829 598 | 1/2015 |

OTHER PUBLICATIONS

International Search Report dated Jul. 1, 2016.
English Translation of Interational Preliminary Report for Application No. PCT/EP2016/000679 dated Jan. 9, 2018.
English Translation of Written Opinion of the Internation Searching Authority for Application No. PCT/EP2016/000679.
Chinese Office Action dated Mar. 19, 2020.
Chinese Office Action dated Jul. 21, 2020.

\* cited by examiner

METHOD FOR MEASURING A PLURALITY OF STATUS PARAMETERS OF A FLUID CONTAINED IN A CONTAINER

BACKGROUND

Field of the Invention

The invention refers to a method for measuring status parameters of a fluid contained in a container. The container is configured for single use and has a wall on which a sensor carrier plate is fixed in a fluid-tight manner. The plate carries sensors that are in operative contact with the internal chamber of the container and are connected for data exchange with an external control unit that receives and processes the measurement data from the sensor.

Description of the Related Art

EP 2 503 320 B1 discloses a bioreactor formed by a disposable bioreactor-bag, i.e., a bag configured as a single-use bioreactor with flexible walls. Such disposable bioreactor-bags find increasing use in production processes in the biochemical and pharmaceutical industry. Compared to earlier usually rigid and reusable containers, the disposable bags, also called single-use-bags have great advantages in relation to hygiene and efficiency as well as flexibility of processes. However, the task of monitoring of the reaction processes taking place inside the bag is not without problems. This is always achieved by suitable sensors, such as electrochemical sensors, thermal and conduction sensors, optical and optical-chemical sensors, etc. For each specific reaction process inside the bag, special sensors have to be provided for its monitoring.

EP 2 829 598 A2, by analogy with the also previously used technique with rigid containers, discloses disposable bioreactor-bags with standardized ports that provide an interface between the inner space of the bag and the outside of the bag, and in which, suitable sensors are inserted, if required. Their sensor head then protrudes inside the bag to provide the contact with the fluid inside the bag, required for the particular measuring process. The sensor part lying outside of the bag forms the interface to a communications path towards an external control unit. This communication path may be provided by an electrical cable, a fiberglass cable or wirelessly, for example, in the form of a radio or IR-connection. The sensor and an external control unit thus are connected to each other for data exchange, so that data generated by the sensor head of the analog or digital type are transmitted via the communication path to the control unit and may there be subject to further processing. This publication discloses a mechanical interface, such as a so called multi-port with a plate that is provided in the bag wall by material fit with a plurality of single apertures, into which the sensors required for the special reaction processes are inserted. The step of inserting a sensor in one of the ports however appears to be critical, because of hygienically relevant aspects, such as ensuring the sterility of the bag's inside. Herein, the risk may exist, that in case of incorrect handling, polluting substances may penetrate the bag interior and contaminate the fluid.

Economical sensors have been developed and are suitable for a single-use. Thus, it has become possible to provide the disposable container with disposable sensors that are provided in a non releasable way on a sensor carrier plate that is connected in a fluid-tight manner—for example, by material-fit connection, such as gluing or welding, or also by suitably pressing or form-fitting connection- to the wall. The disposable containers may be bags with flexible walls or so called "Carboy"-containers made of plastics with rigid walls. The packaging, i.e., the provision of an individual disposable container with an individual combination of different sensors may then take place, in hygienically optimized conditions and by preserving the sterility of the container inner space by the manufacturer of the bag according to standard norms or to special customers requests. Corresponding disposable bioreactor-bags are known from the above mentioned prior art EP 2 503 320 B1. Herein, however, there is a problem, in that the sensors cannot be replaced, which, in case of a sensor defect, may lead to the rejection of the entire bag, including its costly contents. This is more upsetting, if it should subsequently be determined, that no sensor defect was actually present, but only a deviation in the reaction process that could be corrected, but that has led to measuring values suggestive of a sensor defect.

The object of the invention is to provide a method that reduces losses caused by actual or apparent sensor defects.

SUMMARY

This object is achieved in that the sensor plate of at least one of the sensors carries a temporarily inactive duplicate that is then activated if measurement data of the sensor are classified as atypical in the context of an integrity or plausibility test carried out by an external control unit.

The cost-effective production of modern disposable sensors allows the repeated construction of individual sensors of a larger sensor field, without the total price of a corresponding disposable container, such as a one-way-bioreactor or one-way-mixing container in the form of a bag or rigid "Carboy"-container, being therefore substantially increased. According to the invention, therefore, for at least one of the sensors of the sensor field, preferably for a plurality of sensors of the sensor field, and particularly preferred, for all sensors of the sensor field, a respective duplicate is provided that is not necessarily required for the correct measurement of status parameters of the fluid in the container, such as a disposable bioreactor-bag or a disposable mixing container. The duplicates thus are used only as reserve-sensors, which, in case of a defect in the respective main sensor, may be used, without the need for the production process to be interrupted or endangered by a complex sensor replacement. Thus, a mechanical and electronic "superstructure" is provided, in the sense of a redundancy of sensors, the additional costs of which are however more than compensated by the increase in production safety.

As already previously explained, it isn't always easy to differentiate an actual sensor defect from a temporary and correctable deviation of the production process. In the following, various strategies are thus offered, for a rational use of the provided reserve-sensors. The precondition of any kind of reasonable use is however that exceptional situations, which may be caused by a sensor defect or process deviations, are always detected. According to the invention it is thus additionally foreseen, that the external control unit continually, periodically or sporadically subjects the measurement data obtained by the main sensors to integrity or plausibility tests. Such an integrity or plausibility test may comprise, for example, a comparison between current measurement data and reference data that either are stored or calculated from other measurement data. In the simplest case, a list of reference values to be obtained at given points in time is stored. These values then are compared, at the given points in time, with the current effective measurement data. In a more complex case, it is however also possible to provide deductions for certain additional parameters of the fluid, which, per se, cannot be measured or are very difficult to measure, based on measurement data of one or more first sensors, in the disposable container, and to compare the prognosticated parameter values to actual measurement values of second corresponding sensors. Furthermore, it is also possible to use current measurement data from a parallel running reference process as reference values or as a basis for the calculation of reference values. The concrete embodiment of the integrity or plausibility tests has to depend from the concrete form of the respective reaction process. The result of such an integrity test is in any case the decision, whether or not an exceptional situation is present, and the presence of an exceptional situation may then activate one of correction strategies explained in the following.

As an example, in a first embodiment of the invention, the control unit temporarily processes the measurement data received both from the sensor and from the duplicate. In other words, the main sensor and its duplicate operate in parallel for a certain period of time. If the processing of the measurement data received from the sensor and from the duplicate lead to the same results, within a predetermined tolerance, it may be foreseen, that the duplicate is deactivated again. In fact, if the sensor and the duplicate provide essentially the same measurement data, it may be surmised that the exceptional situation recognized by the integrity test is not the result of a sensor defect. The probability that both the sensor and the duplicate are defective, and that they both provide the same false measurement data, may be considered very low. In such an exceptional situation caused by a process deviation, it is preferred to deactivate the duplicate and not the main sensor again. This is considered advantageous in particular on the background of a maximum data consistency. One skilled in the art will notice that in this case, to eliminate the exceptional situation, process-linked measures are required to correct the process deviation that has led to the recognized exceptional situation.

In an elaboration of this first embodiment, in the case that the processing of measurement data received from both the sensor and the duplicate provides results that are different by taking into account the predetermined tolerance, the sensor is deactivated. In other words, if the sensor comparison leads to the result, that the exceptional situation recognized by the plausibility test is due to a defect of the main sensor, the defect sensor is switched off, and the process is continued using the duplicate. In this case there is no need for process-related measures.

As an alternative to the first embodiment of the inventive method, according to a second embodiment it may be foreseen, that the control unit processes the measurement data received from the duplicate, instead of the measurement data received from the sensor. This variant follows the approach that dictates that for each recognized exceptional situation, a switching over from the main sensor to the backup sensor has to take place as a precautionary measure. In this way, a double reception and double processing of measurement data are avoided. However, in this variant, particular measures have to be initiated for differentiating between a sensor defect and a process deviation. In an elaboration of this embodiment it is thus proposed that in the case that the processing of the measurement data received from the duplicate and before activation of the duplicate, from the sensor, provides the same results within a predetermined tolerance, the sensor is reactivated and the duplicate is deactivated. In other words, the current measurement data provided by the duplicate are compared with the measurement data provided by the main sensor immediately before the switching over. If these coincide, i.e., if the duplicate also shows the presence of an exceptional situation, it may be deduced that the exceptional situation recognized by the integrity test is based on a process deviation, and not on a sensor defect. In this case it is considered advantageous, for data consistency reasons, to switch back to the main sensor and to introduce suitable process-related measures for correcting the process deviation.

In an alternative embodiment of the inventive method, if the processing of measurement data received from the duplicate, on one hand, and of measurement data received from the sensor prior to duplicate activation, on the other hand, provides the same results within a predetermined tolerance, the sensor is deactivated and the duplicate is activated. In other words, in this embodiment, the switching over takes place from the main sensor to the backup sensor.

In an advantageous elaboration of the invention, which is independent from the special embodiment of above described method variants for redundancy use, a plurality of sensors of the sensor field are used together for providing a so called "soft sensor". Herein it is envisaged that for a status parameter, which cannot be directly measured by any of the sensors, a parameter value is calculated by the control unit based on measurement data provided by a plurality of different sensors. There are for example important status parameters, such as the proportion of biomass in the fluid, for which no direct sensory system is provided. However, based on the knowledge of different process parameters and of the measurement data of a plurality of sensors, for example an $O_2$ sensor, a $CO_2$ sensor, a sensor for the optical density of the fluid, etc., the desired parameter may be determined through calculations. A plurality of individual sensors thus interacts as a complex "Soft Sensor" for the complex status parameter.

Preferably, the container used for the inventive method may be a disposable bioreactor or a disposable mixing container, which may be provided in the form of bags with a wall, which is flexible at least in segments, or a plastic container ("Carboy") with a wall which is at least partially rigid.

Further characteristics and advantages of the invention may be obtained from the following particular description and from the drawings.

DETAILED DESCRIPTION

Figure 1:
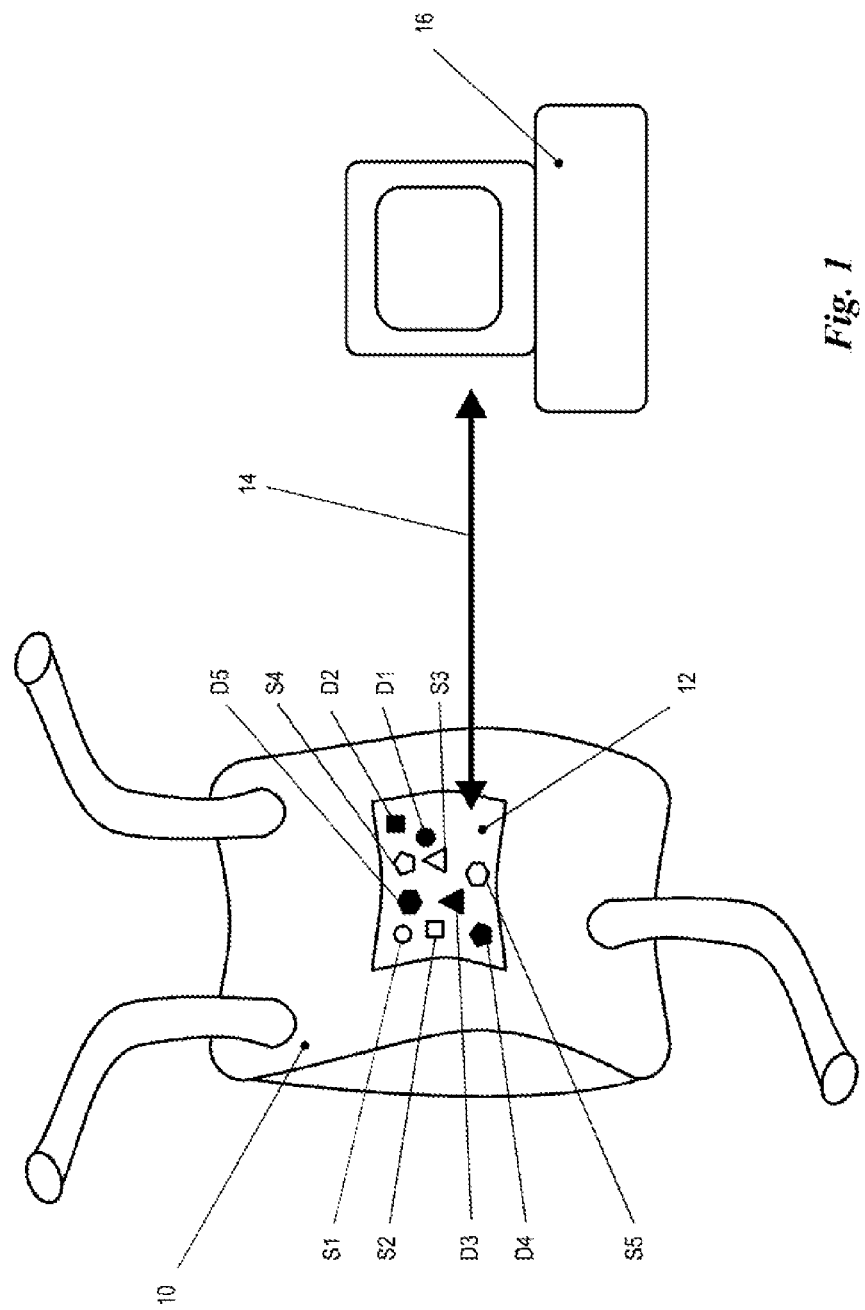
FIG. 1 shows a schematic representation of a container, which is connected to an external control unit.

FIG. 1 is a schematic representation of a container, such as a disposable bioreactor bag or a disposable mixing container 10 that carries a sensor region 12. The sensor region 12 comprises a carrier plate, not shown that is connected in a fluid-tight manner to the wall of the container 10, and that is welded to the bag wall. In other embodiments of the invention, the connection may also be a force-fit connection or a form-fit connection; it is only important that the connection provides the tightness to fluids. Sensors S1-S5 are arranged on the carrier plate and operatively contacts a sensor head, not shown, in the inner space of the bag, in particular a fluid provided inside the bag. Each sensor S1-S5 also is connected via a communication path that is indicated generally by communication arrow 14 to an external control unit 16. Data and control commands may thus be exchanged through the communication path 14 between the external control unit 16 and sensors S1-S5. The communication path 14 may be cabled, such as an electrical cable and/or an optical fiber cable. Alternatively, or additionally, at least one of sensors S1-S5 may be connected wirelessly, in particular over a radio or IR link, to the external control unit 16. The sensors S1-S5 have different measurement tasks, the type of which is not important for the present invention. Their different form is however shown in FIG. 1 by a different shaping of sensors S1-S5.

Moreover, the sensor region 12 comprises duplicates D1-D5 that are constructively identical to sensors S1-S5 that are associated respectively to one of sensors S1-S5 (indicated by the same shape in FIG. 1). The duplicates D1-D5 also are connected through the communication path 14 to the external control unit 16.

Figure 2:
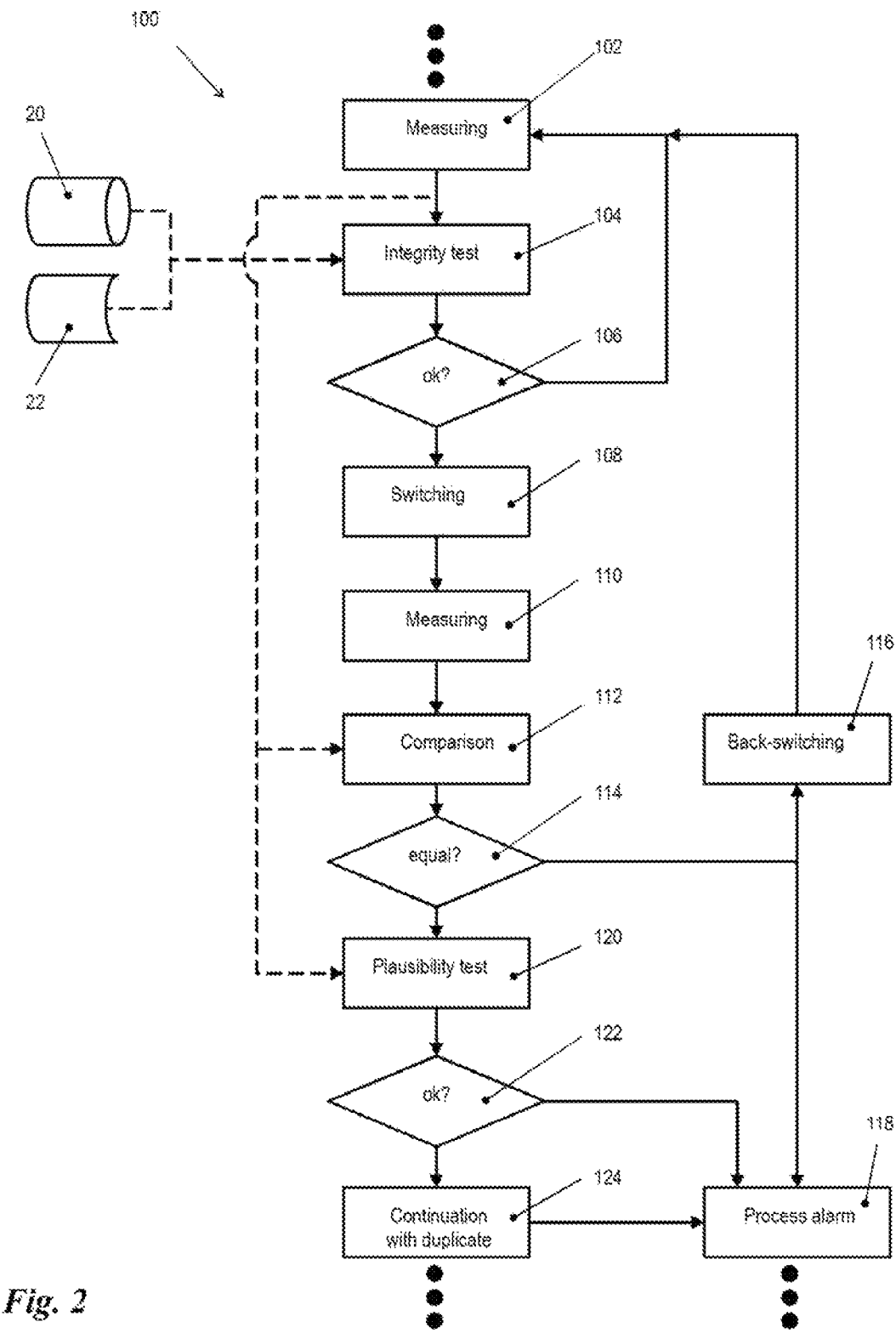
FIG. 2 shows a flow chart illustrating an embodiment of the inventive method.

FIG. 2 shows a greatly simplified flow chart of a preferred embodiment of the inventive method. For the sake of clarity, FIG. 2 shows only the method pertaining to one of sensors S1-S5. However, one skilled in the art will recognize that the same method or a similar method may be used for each one of sensors S1-S5.

After the usual and required initialization routines have been performed and a process in the container 10 (for example a disposable bioreactor bag or a disposable mixing container) is steadily proceeding, at step 102 of method a certain status parameter of the fluid in the container 10 is measured by means of an associated sensor. The corresponding measured value is subject in step 104 to an integrity test, wherein reference values 20 stored to this end and/or measurement data 22 from a reference process run in parallel are used as comparison values. If the current measured values in step 104 pass the integrity test, i.e., they lie within a predetermined tolerance around the nominal values to be reached, the method 100 branches at decision step 106 back to the measurement step 102.

If, on the contrary, the current measurement data do not pass the integrity test at step 104, the sensor that has provided the atypical measurement data is switched off at step 108 and the respective duplicate is activated. In other words, at step 108, the switch over from the sensor to its duplicate takes place. Then, at step 110, the measurement is repeated by means of the duplicate. Alternatively, both the sensor and its duplicate may provide measurement results in parallel, i.e., the sensor is not deactivated, but the measurement results provided by the sensor are not subject to further processing, while only the results provided by the duplicate are processed.

The measurement result provided by the duplicate at step 110 is compared at step 112 with the result provided by sensor at step 102. If both measurement results are identical or within a predetermined tolerance, then the method 100 branches at decision step 114 to step 116, where a back-switching from the duplicate to the original sensor occurs. In fact, the equivalence of the measurement results from the comparison at step 112 means that the atypical measurement values are not due to a sensor defect, but much more probably to a process deviation. Thus, there is no reason to perform future measurements without the original sensor. The back-switching to the original sensor could obviously also be omitted, while the duplicate remains active, since the comparison at step 112 also proves the correct operation of duplicate. Due to reasons of data consistency it is however more advantageous to essentially use the same sensor for the whole process.

However, in this case, the atypical measured values hint at a very probable process deviation, so that at step 118, simultaneously, a process alarm is issued to initiate the introduction of repairing routines or the intervention by an operator. The precise measures to be taken following the process alarm at step 118 depend from the process configuration, the type and value of the deviation of the status parameter and the technical conditions of the particular plant. This is indicated in FIG. 2 by the continuation points at step 118.

If, however, the comparison at step 112 indicates that the measurement values of sensor and its duplicate differ from each other beyond the predetermined allowed tolerance, then method 100 branches at decision step 114 to step 120, where the data generated by the duplicate are subject to a plausibility test. In fact, a double sensor defect could be hypothesized, i.e., a defect of the sensor and of its duplicate, wherein due to probability considerations, it may be substantially excluded, that both defective sensors provide identical values. It is thus sufficient to perform a plausibility test at step 120. It is also possible to interpose a similar plausibility test between the decision step 114 and the back-switching step 116. The plausibility test at step 120, as well as the integrity test at step 104, may use the reference values 20, 22 and/or further process-depending measurement and setup-data.

If the measurement data generated by the duplicate pass the plausibility test at step 120, i.e., if they lie within the expected values, the method 100 branches at decision step 122 to method step 124, where the production process is continued without further interventions, wherein in the following only the duplicate is used instead of the sensor, which has been recognized to be defective. At the same time, however, according to step 118 a process alarm is issued and is only used for indicating that the duplicate is used instead of the sensor. Such a process occurrence usually is indicated in the process protocol.

If the plausibility test at step 120 shows, on the contrary, that the measurement values provided by the duplicate are also either incorrect or, although correct, demonstrate a process deviation, the process 100 branches out, at decisional step 122, without delay, to process alarm according to step 118. In this case, important measures have to be introduced. In particular it is then necessary to verify, if the atypical measurement values of the duplicate are the result of a duplicate error or the result of an actual process deviation. In case of a process deviation, corrective measures may be introduced. In case of a defect of the duplicate, the entire process normally has to be stopped, since after the failure of a sensor and of its duplicate, the corresponding status parameter cannot be measured anymore. One skilled in the art will understand, based on this context, that it is fundamentally also possible to provide more than one duplicate for each sensor, so that before the interruption of the process, in a similar way to the above description, the switch over to a further duplicate may take place.

The embodiments discussed in the specific description and shown in the figures are obviously only illustrative examples of embodiments of the present invention. One skilled in the art is provided with a wide spectrum of possible variations, based on the present disclosure.

REFERENCE LIST 10 container
12 sensor region
S1-S5 sensor at 12
D1-D5 duplicate of S1-S5
14 communication path
16 external control unit
20 reference data
22 reference measurement values
100 method
102 step
104 step
106 decision step
108 step
110 step
112 step
114 decision step
116 step
118 step
120 step
122 decision step
124 step

The invention claimed is:

1. A method for measuring a plurality of status parameters of a fluid contained in a container (10), the container (10) being configured for a single use and has a wall on which a sensor carrier plate is fixed in a fluid-tight manner, the sensor carrying plate carrying a plurality of sensors (S1-S5, D1-D5) that are disposed and configured to be operative contact with an internal space of the container (10) and are connected for data exchange (14) with an external control unit (16) that receives and processes measurement data from the sensors (S1-S5, D1-D5), the sensors carried by the sensor carrier plate include at least one pair of sensors (S1-S5) that includes a first sensor (S1-S5) and a duplicate (D1-D5) of the first sensor (S1-S5), the method comprising:

operating the external control unit (16) to carry out an integrity or plausibility test using the measurement data of at least the first sensor (S1-S5) while keeping the duplicate (D1-D5) of the first sensor (S1-S5) in a temporarily inactive state;

determining if the measurement data of at least the first sensor (S1-S5) is atypical in the context of the integrity or plausibility test carried out by the external control unit (16);

activating the duplicate (D1-D5) of the first sensor (S1-S5) if the measurement data of the first sensor (S1-S5) is determined to be atypical in the context of the integrity or plausibility test carried out by the external control unit (16); and determining whether processing of the measurement data received from the first sensor (S1-S5) and from the duplicate (D1-D5) of the first sensor provides the same results within a predetermined tolerance.

2. The method of claim 1, further comprising:

operating the control unit (16) to temporarily processes both the measurement data received from the first sensor (S1-S5) and the measurement data received from the duplicate (D1-D5) of the first sensor.

3. The method of claim 1, further comprising:

deactivating the duplicate (D1-D5) of the first sensor if the processing of the measurement data received from the first sensor (S1-S5) and from the duplicate (D1-D5) of the first sensor provides the same results within a predetermined tolerance.

4. The method of claim 3, further comprising:

deactivating the first sensor (S1-S5) if the processing of the measurement data received from the first sensor (S1-S5) and from the duplicate (D1-D5) of the first sensor provides different results in consideration of the predetermined tolerance.

5. The method of claim 1 further comprising:

using the control unit (16) to process the measurement data received from the duplicate (D1-D5) of the first sensor instead of the measurement data received from the first sensor (S1-S5) if the measurement data received from the first sensor (S1-S5) and from the duplicate (D1-D5) of the first sensor provides the same results within a predetermined tolerance.

6. The method of claim 5, further comprising:

reactivating the first sensor (S1-S5) and deactivating the duplicate (D1-D5) of the first sensor if the processing of the measurement data received from the duplicate (D1-D5) of the first sensor and of the measurement data received, prior to activation of the duplicate (D1-D5), from the first sensor (S1-S5) provide the same results within a predetermined tolerance.

7. The method of claim 1, further comprising:

calculating a parameter value by the external control unit, based on measurement data of a plurality of different sensors for a status parameter that cannot be directly measured by any of the sensors.

8. The method of claim 1, wherein the container is a disposable bioreactor or a disposable mixing container.

9. The method of claim 8, wherein the disposable bioreactor or the disposable mixing container are bags with a wall that has flexible segments, or as a plastic container, with a wall that has rigid segments.

* * * * *